(12) United States Patent
Prasad et al.

(10) Patent No.: US 7,368,593 B1
(45) Date of Patent: May 6, 2008

(54) METHOD OF SELECTIVE ESTERIFICATION

(75) Inventors: Ramanujam Prasad, Streamwood, IL (US); Jeffrey P. Conrad, Chicago, IL (US); Thaddeus J. Ilg, Chicago, IL (US)

(73) Assignee: Organics L.L.C., Northbrook, IL (US)

( * ) Notice: Subject to any disclaimer, the term of this patent is extended or adjusted under 35 U.S.C. 154(b) by 462 days.

(21) Appl. No.: 10/920,514

(22) Filed: Aug. 18, 2004

Related U.S. Application Data

(60) Provisional application No. 60/495,904, filed on Aug. 18, 2003.

(51) Int. Cl.
*C07C 69/88* (2006.01)
(52) U.S. Cl. ........................................ 560/67
(58) Field of Classification Search ............... 560/67
See application file for complete search history.

(56) References Cited

U.S. PATENT DOCUMENTS

| | | | | |
|---|---|---|---|---|
| 5,008,441 A | 4/1991 | Nakanishi et al. | ............ | 560/75 |
| 5,591,773 A | 1/1997 | Grunberger et al. | ........ | 514/532 |
| 5,610,185 A | 3/1997 | Stanwell et al. | ............ | 514/544 |
| 5,945,446 A | 8/1999 | Laub | .......................... | 514/456 |
| 2002/0188021 A1 | 12/2002 | Koumenis et al. | .......... | 514/513 |

OTHER PUBLICATIONS

Aldrich, p. 651,885, 1998-1999, p. 3.*
Lee et al ,An Improved method for preparation of Carboxylic esters using CsF-Celite/alkyl halide/CH3CN,Synthetic Comm., 1998,28(1), 2021-2026.*
Aldrich, 1998-1999, p. 1160.*
Aldrich, p. 1619, 1998-1999, p. 2.*
"Caffeic Acid Phenethyl Ester (CAPE): Synthesis and X-Ray Crystallographic Analysis," Son et al, *Chem. Pharm. Bull.*, vol. 49, No. 2, pp. 236-238 (2001).
"Hydroxylated Aromatic Inhibitors of HIV-1 Integrase," Burke et al., *J. Med. Chem.* vol. 38, pp. 4171-4178 (1995).
"Inhibitory Effect of Caffeic Acid Phenethyl Ester on Human Leukemia HL-60 Cells," Chen et al., *Cancer Letters*, vol. 108, pp. 211-214 (1996).
"Preferential Cytotoxicity on Tumor Cells by Caffeic Acid Phenethyl Ester Isolated from Propolis," Grunberger et al., *Experientia*, vol. 44, pp. 230-232 (1988).
"Synthesis of Two Allergenic Constituents of Propolis and Poplar Bud Excretion," Hashimoto et al., *Z. Naturforsch*, vol. 43c, pp. 470-472 (1988).
Report on Carcinogens, Eleventh Edition; U.S. Department of Health and Human Services, Public Health Service, National Toxicology Program, entry for Hexamethylphosphoramide (Jan. 31, 2005).

* cited by examiner

*Primary Examiner*—Taylor Victor Oh
(74) *Attorney, Agent, or Firm*—Marshall, Gerstein & Borun LLP

(57) ABSTRACT

A method of preparing a compound of formula I

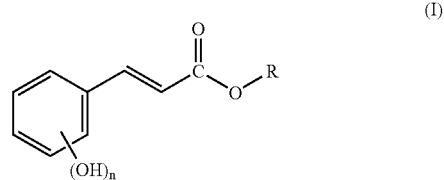

wherein R is a hydrocarbon and n is an integer from 1 to 5, including the steps of: contacting a compound of formula II

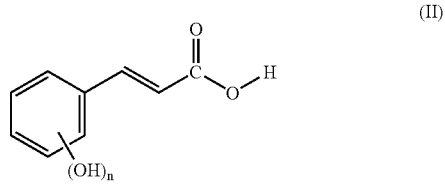

with a compound selected from the group consisting of amines, and carbonates, bicarbonates, and hydroxides of alkali metals, and combinations thereof, in a solvent to produce a salt of a compound of formula II; treating the salt of the compound of formula II in a polar, aprotic solvent with an organic halide having a formula R—X, wherein X is selected from chlorine, bromine, iodine, and combinations thereof, to produce an ester of formula I; isolating a reaction product including the ester of formula I from the solvent by precipitation or solvent extraction; and purifying the compound of formula I, is disclosed.

33 Claims, No Drawings

METHOD OF SELECTIVE ESTERIFICATION

CROSS-REFERENCE TO RELATED APPLICATION

The benefit under 35 U.S.C. §119(e) of U.S. Provisional Patent Application Ser. No. 60/495,904 filed Aug. 18, 2003, is hereby claimed.

BACKGROUND

1. Field of the Disclosure

The disclosure relates generally to selective esterification. More particularly, the disclosure relates to selective esterification of a carboxylic acid functional group in the presence of phenolic functional groups.

2. Brief Description of Related Technology

The honeybee hive product propolis is a folk medicine employed for treating various ailments. Many important pharmaceutical properties have been ascribed to propolis, including anti-inflammatory, antiviral, immunostimulatory, and carcinostatic activities. See, for example, Kujmgiev et al., Pharmazie, vol. 48, p. 785 (1993); Focht et al., Arzneim.-Forsch., vol. 43, p. 921 (1993); and Khayyal et al., Drugs Under Exp. Clin. Res., vol. 19, p. 197 (1993). Propolis extracts have provided an active component identified as caffeic acid phenethyl ester (CAPE), which is a carboxylic acid ester with two free phenolic hydroxyl groups. An individual study on CAPE has shown that it inhibits growth of prostate cancer in cell cultures. Differential cytotoxicity has been observed in normal rat/human versus transformed rat/human melanoma and breast carcinoma cell lines in the presence of CAPE. See Grunberger et al., Experientia, vol. 44, p. 230 (1988).

Nakanishit et al., U.S. Pat. No. 5,008,441 (Apr. 16, 1991), Burke et al., J. Med. Chem., vol. 38, p. 4171 (1995); and Stanwell et al. U.S. Pat. No. 5,610,185 (Mar. 11, 1997) describe the esterification of caffeic acid with phenethyl alcohol by refluxing the two reagents in the presence of p-toluenesulfonic acid in benzene. The product CAPE was obtained in about 40% yield after chromatography.

Hashimoto et al., Z. Naturforsch. vol. 43c, p. 470 (1988) and Son et al., Chem. Pharm. Bull. vol. 49(2) p. 236 (2001) describe the sodium salt of caffeic acid with phenethyl bromide in hexamethylphosphoramide (HMPA) to synthesize CAPE. Yields up to 70% were reported, although HMPA is reasonably anticipated to be a human carcinogen and once again a chromatography step is required for the purification.

Dicyclohexylcarbodiimide (DCC) is another reagent which has been used for esterification of caffeic acid with alcohol under mild conditions. See Chen et al., Cancer Letters, vol. 108, p. 211 (1996). However, this process also required chromatographic purification, and resulted in only about 38% yield.

SUMMARY

One aspect of the disclosure provides a method of preparing a compound of formula I

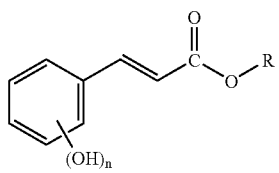

wherein n is an integer from 1 to 5, including the steps of: treating a salt of a compound of formula II

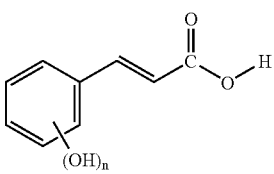

in a polar, aprotic solvent with an organic halide having a formula R—X, to produce an ester of formula I; and isolating a reaction product including the ester of formula I from the solvent. The method can be followed by a purification step. The method can optionally include the step of contacting a compound of formula II with a compound selected from the group consisting of amines, and carbonates, bicarbonates, and hydroxides of alkali metals, and combinations of any of the foregoing, in a solvent to produce the salt of a compound of formula II. The method can also optionally include the use of a phase transfer catalyst.

Further aspects and advantages may become apparent to those skilled in the art from a review of the following detailed description. While the method is susceptible of embodiments in various forms, the description hereafter includes specific embodiments with the understanding that the disclosure is illustrative, and is not intended to limit the invention to the specific embodiments of the method described herein.

DETAILED DESCRIPTION

The compounds of formula II

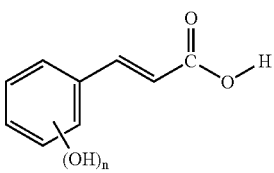

have from one to five phenolic hydroxyl groups (n=1, 2, 3, 4, or 5) and one carboxylic acid group. In one embodiment, the compound of formula II is caffeic acid. According to the method disclosed herein, selective esterification of the acid function (i.e., with little or no etherification of phenolic hydroxyl groups) is achieved. The method described herein is also an industrially suitable procedure for the synthesis and isolation of the required product that permits the elimination of chromatographic separation and permits the use of low hazard, cost effective solvents. In a preferred embodiment, the ester of formula I is produced without the use of chromatographic separation, which can be a costly, tedious, and inefficient method for commercial production.

Generally, a salt of a compound of formula II is treated with an appropriate halide in a polar, aprotic solvent for a suitable amount of time, followed by isolation and, optionally, purification to yield the desired ester. Sodium, potassium, lithium, and amine salts of a compound of formula II are preferred. The salt of the compound of formula II is formed at the carboxlyic acid group of the compound of formula II, for example as shown in the sodium salt illustrated below:

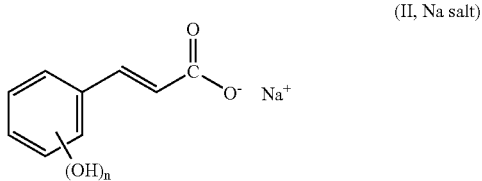

(II, Na salt)

The polar, aprotic solvent is suitable for industrial applications and preferably has a relatively low hazard rating, such that the solvent can be used to produce a product intended for human consumption. Preferably, the solvent is non-genotoxic.

Thus, in one embodiment, the polar, aprotic solvent is rated Class 2 ("non-genotoxic animal carcinogens or possible causative agents of other irreversible toxicity such as neurotoxicity or teratogenicity") or greater in the International Conference on Harmonization of Technical Requirements for the Registration of Pharmaceuticals for Human Use (ICH)/Therapeutic Products Program (TPP) guideline, "Impurities: Guideline for Residual Solvents," more preferably Class 3 ("solvents with low toxic potential"). For purposes of such an embodiment, class 2 of the ICH guideline is interpreted herein to exclude solvents reasonably anticipated to be human carcinogens.

In another embodiment, the polar, aprotic solvent has a modulus of molecular dipole moment less than 4.19 debye, preferably less than about 4.1 debye, and more preferably less than about 4.0 debye. In another embodiment, the polar, aprotic solvent has a dielectric constant higher than 30.

Examples of suitable polar, aprotic solvents include N,N-dialkylacylamides such as dimethylformamide (DMF) and dimethylacetamide; amines such as pyridine; dimethylsulfoxide (DMSO); and N-methylpyrrolidone. A preferred solvent for synthesizing caffeic acid phenethyl ester is DMSO.

Halides for use in the method include halides with hydrocarbons, such as $C_1$-$C_{18}$ halides, preferably alkyl, arylalkyl, cycloalkyl, alkenyl, and cycloalkenyl. Particularly preferred are alkyl and arylalkyl, such as methyl, ethyl, butyl, hexyl, and phenethyl halides. Preferred halogens are chlorine, bromine, and iodine.

The ratio of halide to acid has an effect on yield and purity of the resulting product. As the ratio of halide to acid is decreased below equimolar, the yield decreases and acid (or salt) reagent is wasted. As the ratio of halide to acid is increased substantially above equimolar, the product quality is not significantly improved, but halide reagent is wasted. Accordingly, the ratio of halide to acid preferably is in a range of about 0.5:1 to about 5:1, more preferably approximately equimolar to about 2:1.

A phase transfer catalyst can optionally be employed to enhance the reactivity of a salt of a compound of formula II. A phase transfer catalyst enhances the solubility of the anion of the salt of a compound of formula II allowing it to react in the organic liquid phase containing the halide. Suitable phase transfer catalysts include quaternary ammonium and phosphonium salts as well as crown ethers and other cryptands. The ratio of catalyst to a salt of a compound of formula II can be small since each molecule of catalyst can act upon numerous molecules of salt. A molar ratio of about 0.001 to about 0.1 (catalyst to salt) is preferred.

The reaction temperature for esterification effects the reaction kinetics and production of impurities. As the temperature decreases below room temperature, the reaction proceeds very slowly. As the temperature increases, the reaction rate increases, but production of impurities also can increase. Accordingly, the reaction temperature is preferably in a range of about 10° C. to about 150° C., more preferably about room temperature to about 110° C., or about 60° C. to about 80° C., such as about 70° C.

Isolation of the product can be achieved by any suitable method, such as precipitation, extraction, distillation, or any combination thereof. Precipitation or solvent extraction are preferred.

In an embodiment of the method whereby an extraction method is used to isolate the product, the use of cold water and/or a dilute aqueous acid can be useful for reducing or avoiding hydrolysis of the ester under alkaline conditions, if present. Preferred extraction solvents dissolve the product compound of interest and are immiscible with water. Particularly preferred extraction solvents are those suitable for industrial applications and that preferably have a relatively low hazard rating. Preferably, the solvent is non-genotoxic.

Thus, in one embodiment, the extraction solvent is rated Class 2 or greater, preferably 3, in the International Conference on Harmonization of Technical Requirements for the Registration of Pharmaceuticals for Human Use (ICH)/Therapeutic Products Program (TPP) guideline, "Impurities: Guideline for Residual Solvents," more preferably Class 3. For purposes of such an embodiment, class 2 of the ICH guideline is interpreted herein to exclude solvents reasonably anticipated to be human carcinogens.

Suitable extraction solvents include methyl acetate, ethyl acetate, butyl acetate, methylene chloride, ethylene chloride, methyltetrabutylether (MTBE), and diethylether. Ethyl acetate is preferred. Following extraction, the organic extract, or combined organic extracts are preferably washed with water, or optionally a solution of a dilute aqueous acid or base, to neutralize residual base or acid, respectively.

Excess solvent is removed from the precipitate or extraction product to yield a residue. In a preferred method, the extraction product is first dried (e.g., over sodium sulfate or magnesium sulfate) and then the solvent is removed (e.g., by vacuum distillation).

Although the method yields a residue of relatively high purity, the crude residue can be purified by treatment with a suitable solvent, and optionally crystallized without the need for chromatographic separation. Suitable treatments include washing, slurry purification, crystallization, and combinations thereof. Preferred solvents include hydrocarbon solvents such as toluene, and combinations of solvents (e.g., ethyl acetate, ether, tetrahydrofuran (THF), acetone, water, methanol, ethanol, hexane, and heptane). Toluene is preferred. For example, purification of the ester product can involve digestion of the crude residue in boiling toluene with activated carbon and filtering (e.g., gravity filtration) the hot solution. On cooling the filtrate, the product crystallizes out.

A preferred method for preparing a salt of a compound of formula II includes contacting the compound of formula II with an alkali metal compound, amine, or both, in a suitable solvent. The order of addition is not important. Thus, the compound of formula II can be combined with a solid alkali metal compound and then added to water, for example. In another embodiment, the compound of formula II is dissolved in a polar, aprotic solvent, and then one or more alkali metal compounds or amines are added. In another embodiment, the compound of formula II is dissolved in a polar, aprotic solvent, and then an aqueous solution including one or more alkali metal compounds or amines are added. In another embodiment, the compound of formula II is contacted (e.g., combined) with a solid alkali metal compound then water is added, and then a low hazard, polar, aprotic solvent is added to proceed with the esterification process.

The alkali metal compound preferably is one or more of a carbonate, bicarbonate, and hydroxide of an alkali metal, or mixtures thereof. Sodium, potassium, and lithium are preferred alkali metals, and mixtures thereof can be used. The preferred amine compound can be selected from one or more amines that will not consume the halide reagent, such as one or more compounds selected from the group consisting of trialkylamines (e.g., triethylamine, trimethylamine), triarylamines (e.g., triphenylamine, trinaphthylamine), dialkylarylamines, diarylalkylamines (e.g., 1,8-bis(dimethylamino)naphthalene, N,N-dimethylaniline), and imidazoles (e.g., 1-methyl imidazole). Trisubstituted amines are preferred. Preferred low hazard, polar, aprotic solvents for use in preparing a salt of a compound of formula II are those described above in connection with the esterification step.

The molar ratio of the compound of formula II to base can vary. As the ratio of acid to base is increased, less salt is produced and the compound of formula II is wasted. As the ratio of acid to base is reduced, the potential for side reactions increases. Accordingly, the molar ratio of compound of formula II to base preferably is in a range of about 1:0.5 to about 1:5, and more preferably in a range of about 1:1 to about 1:2.

As used herein, aprotic solvents are solvents which have no ability, or only a weak ability, to liberate protons.

As used herein, the term "alkyl" includes straight chained and branched hydrocarbon groups containing the indicated number of carbon atoms, typically methyl, ethyl, propyl, and butyl groups. The term "alkyl" also includes "bridged alkyl," e.g., a $C_4$-$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic hydrocarbon group, e.g., cyclopropyl, cyclobutyl, cyclohexyl, and cyclopentyl.

As used herein, the term "alkenyl" is defined identically as "alkyl," except for containing a carbon-carbon double bond. The term "cycloalkenyl" is identical to "cycloalkyl" except containing a carbon-carbon double bond, e.g., cyclopropyl, cyclobutyl, cyclohexyl, and cyclopentyl.

As used herein, the term "aryl," alone or in combination, is defined herein as a monocyclic or polycyclic aromatic group, preferably a monocyclic or bicyclic aromatic group, e.g., phenyl or naphthyl, optionally substituted with one or more alkyl or alkoxy groups.

EXAMPLES

The following examples are provided for illustration and are not intended to limit the scope of the invention.

Example 1

1.98 g of caffeic acid was dissolved in 100 mL of dimethylformamide. 2.28 mL of 25% aqueous sodium hydroxide solution was added while stirring. Stirring continued for 1 hr. At the end of this period a solution of 5.7 mL of phenethyl bromide in 10 mL dimethylformamide was added slowly in 30 minutes. The resulting reaction mixture was stirred at room temperature for 50 hrs. Next, the reaction mixture was poured into 200 mL of water and extracted with ethyl acetate (3×100 mL). The combined organic extract was washed with 100 mL of 1N HCl and water (3×100 mL). After drying over sodium sulfate, the solvent was distilled off under vacuum. The residue was crystallized from ethyl acetate/hexane by treatment with activated carbon to obtain caffeic acid phenethyl ester. The yield was 600 mg and the purity was greater than 90%.

Example 2

1 g of caffeic acid was dissolved in 25 mL of pyridine. 1.14 mL of 25% aqueous sodium hydroxide solution was added while stirring. Stirring continued for 1 hr. At the end of this period a solution of 2.8 mL of phenethyl bromide was added slowly in 30 minutes. The resulting reaction mixture was stirred at room temperature for 50 hrs. Next, the reaction mixture was poured into 100 mL of 10% HCl and extracted with methylene chloride (2×50 mL). The combined organic extract was washed with water (2×50 mL). After drying over sodium sulfate, the solvent was distilled off under vacuum. The residue was crystallized from toluene by treatment with activated carbon to obtain caffeic acid phenethyl ester. The yield was 120 mg and the purity was by TLC single spot.

Example 3

1 g of caffeic acid was dissolved in 25 mL of dimethylsulfoxide. 0.77 mL of 25% aqueous sodium hydroxide solution was added while stirring. Stirring continued for 1 hr. At the end of this period a solution of 1.10 mL of phenethyl bromide was added slowly in 30 minutes. The resulting reaction mixture was stirred at room temperature for 50 hrs. Next, the reaction mixture was poured into 75 mL of cold water and extracted with ethyl acetate (3×60 mL). The combined organic extract was washed with 50 mL of 5% HCl and water (60 mL). After drying over sodium sulfate, the solvent was distilled off under vacuum. The residue was crystallized from toluene by treatment with activated carbon to obtain caffeic acid phenethyl ester. The yield was 760 mg and the purity was greater than 90%.

Example 4

1 g of caffeic acid was dissolved in 20 mL of ethanol and 2 mL water. 0.5 g of sodium bicarbonate was added while stirring. Stirring continued for 3 hr. Solvent and water were distilled off under vacuum. The residual solid was dissolved in 25 mL dimethylformamide and heated to 150° C. To this hot reaction mixture 0.8 mL of phenethyl bromide was added. The resulting reaction mixture was stirred for 40 hrs. Next, the reaction mixture was poured into 75 mL of cold water and extracted with ether (3×70 mL). The combined organic extract was washed with 50 mL of 5% HCl and water (60 mL). After drying over sodium sulfate, the solvent was distilled off under vacuum. The residue was crystallized from toluene by treatment with activated carbon to obtain caffeic acid phenethyl ester. The yield was 304 mg and the purity was greater than 90%.

Example 5

10.0 g of caffeic acid and 6.1 g potassium bicarbonate were mixed in 50 mL of dimethylsulfoxide. 7.6 mL of phenethyl bromide were added and the reaction mixture was heated to 70° C. under agitation. The mixture was stirred for 3 hrs, and then cooled to <25° C. The reaction mixture was slowly added to 500 mL of water under agitation to precipitate the product, which was recovered by filtration. The crude product was washed with dilute potassium bicarbonate and toluene and was then recrystallized via cooling from 200 mL boiling toluene to obtain caffeic acid phenethyl ester The yield was 9.0 g and the assay was 100%.

Example 6

2 g of caffeic acid was dissolved in 50 mL of dimethylsulfoxide. 1.6 mL of triethylamine was added while stirring. Stirring continued for 1 hr. At the end of this period a solution of 1.67 mL of phenethyl bromide was added slowly. The resulting reaction mixture was stirred at room temperature and monitored. Conversion of caffeic acid to Caffeic acid phenethyl ester was about 31% in 41 hrs.

Example 7

1.0 g of caffeic acid was dissolved in 5 mL of dimethylsulfoxide and 0.55 g potassium bicarbonate were added and the mixture was allowed to react for 2 hours at room temperature. 0.75 mL of phenethyl bromide and 0.07 g of benzyl tributyl ammonium chloride were added and the reaction mixture was stirred for 90 hours. The reaction mixture was slowly added to 50 mL of water under agitation to precipitate the product, which was recovered by filtration. The crude product was then recrystallized from 17.5 mL boiling toluene to obtain caffeic acid phenethyl ester The yield was 830 mg and the purity was 97%.

The foregoing description is given for clearness of understanding only, and no unnecessary limitations should be understood therefrom, as modifications within the scope of the invention will be apparent to those having ordinary skill in the art. Throughout the specification, where methods are described as including steps, it is contemplated that the methods can also consist essentially of, or consist of, any combination of the recited steps, and subsets thereof, unless stated otherwise.

What is claimed is:

1. A method of preparing a compound of formula I

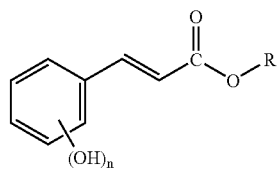

(I)

wherein R is selected from $C_1$-$C_{18}$ hydrocarbons and n is an integer from 1 to 5, comprising the steps of (a) treating a salt of a compound of formula II

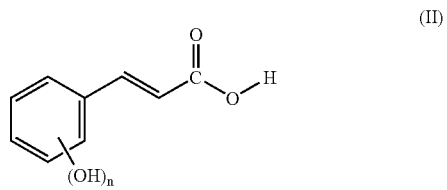

(II)

wherein n is the same as in formula I, in a non-genotoxic, polar, aprotic solvent with an organic halide having a formula R—X, wherein X is selected from chlorine, bromine, iodine, and combinations thereof, to produce an ester of formula I; and (b) isolating a reaction product comprising the compound of formula I from the solvent by precipitation or solvent extraction, wherein said method is independent of a chromatographic separation step.

2. The method of claim 1, wherein R is alkyl, arylalkyl, cycloalkyl, alkenyl, or cycloalkenyl.

3. The method of claim 2, wherein R is alkyl or arylalkyl.

4. The method of claim 1, wherein the compound of formula II is caffeic acid.

5. The method of claim 4, wherein R is phenethyl.

6. The method of claim 1, wherein said isolating step comprises precipitation.

7. The method of claim 1, further comprising the step of purifying the compound of formula I from the reaction product.

8. The method of claim 7, wherein said purification step comprises crystallization.

9. The method of claim 1, wherein said non-genotoxic, aprotic, polar solvent comprises a solvent selected from the group consisting of amines, N,N-dialkylacylamides, dimethylsulfoxide, N-methylpyrrolidone, and mixtures thereof.

10. The method of claim 1, wherein said pharmaceutically acceptable, aprotic, polar solvent has a modulus of molecular dipole moment less than 4.0 debye.

11. The method of claim 10, wherein said pharmaceutically acceptable, aprotic, polar solvent has a dielectric constant of about 30 or greater.

12. The method of claim 1, wherein the molar ratio of said halide to said salt of a compound of formula II is in a range of about 0.5:1 to about 5:1.

13. The method of claim 1, further comprising the steps of contacting a compound of formula II and a compound selected from the group consisting of carbonates, bicarbonates, and hydroxides of alkali metals, and combinations thereof, in a solvent to produce an alkali metal salt of a compound of formula II.

14. The method of claim 13, wherein said solvent comprises water.

15. The method of claim 13, further comprising the steps of dissolving the compound of formula II in a non-genotoxic, polar, aprotic solvent and adding an aqueous solution comprising a compound selected from the group consisting of carbonates, bicarbonates, and hydroxides of alkali metals, and combinations thereof, to said compound of formula II, to produce said alkali metal salt of the compound of formula II.

16. The method of claim 15, further comprising the step of adding a quaternary ammonium salt phase transfer catalyst to one or more of said non-genotoxic, polar, aprotic solvent, said aqueous solution, or the combination thereof.

17. The method of claim 13, wherein said alkali metal is selected from the group consisting of sodium, potassium, lithium, and combinations thereof.

18. The method of claim 13, wherein the molar ratio of said compound of formula II to alkali metal is in a range of about 1:0.5 to about 1:5.

19. The method of claim 1, further comprising the steps of contacting a compound of formula II and an amine in a solvent to produce an amine salt of a compound of formula II.

20. The method of claim 19, wherein said solvent comprises water.

21. The method of claim 19, further comprising the steps of dissolving the compound of formula II in a non-genotoxic, polar, aprotic solvent and adding an aqueous solution comprising an amine to said compound of formula II, to produce said amine salt of the compound of formula II.

22. The method of claim 21, further comprising the step of adding a quaternary ammonium salt phase transfer catalyst to one or more of said non-genotoxic, polar, aprotic solvent, said aqueous solution, or the combination thereof.

23. The method of claim 19, wherein said amine is selected from the group consisting of trialkylamines, triarylamines, dialklylarylamines, diarylaklylamines, imidazoles, and combinations thereof.

24. The method of claim 23, wherein said amine is selected from the group consisting of trialkylamines, triarylamines, dialklylarylamines, diarylaklylamines, and combinations thereof.

25. The method of claim 23, wherein said amine is selected from the group consisting of triethylamine, trimethylamine, 1,8-bis(dimethylamino)naphthalene, and combinations thereof.

26. The method of claim 19, wherein the molar ratio of said compound of formula II to amine is in a range of about 1:0.5 to about 1:5.

27. The method of claim 9, wherein said non-genotoxic, polar, aprotic solvent is selected from the group consisting of dimethylsulfoxide, N-methylpyrrolidone, and mixtures thereof.

28. A method of preparing a compound of formula I

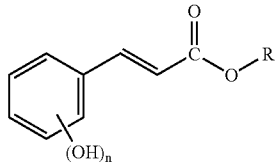

(I)

wherein R is selected from $C_1$-$C_{18}$ hydrocarbons and n is an integer from 1 to 5, comprising the steps of
(a) treating a salt of a compound of formula II

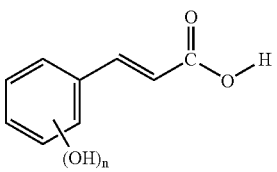

(II)

wherein n is the same as in formula I, in a non-genotoxic, polar, aprotic solvent with an organic halide having a formula R—X, wherein X is selected from chlorine, bromine, iodine, and combinations thereof, to produce an ester of formula I; and
(b) isolating a reaction product comprising the compound of formula I from the solvent;
(c) purifying the reaction product by crystallization from a solvent comprising a hydrocarbon solvent to yield a first purified residue comprising the compound of formula I; and
(d) optionally further purifying the first purified residue by chromatographic separation to yield a second purified residue comprising the compound of formula I, wherein the first purified residue comprising the compound of formula I is greater than 90% pure.

29. The method of claim 28, wherein the hydrocarbon solvent for crystallization comprises a solvent selected from the group consisting of toluene and hexane.

30. The method of claim 29, wherein the hydrocarbon solvent for crystallization comprises toluene.

31. The method of claim 30, wherein the compound of formula II is caffeic acid.

32. The method of claim 29, wherein the hydrocarbon solvent for crystallization comprises hexane and the solvent further comprises ethyl acetate.

33. The method of claim 28, wherein the compound of formula II is caffeic acid.

* * * * *

UNITED STATES PATENT AND TRADEMARK OFFICE
CERTIFICATE OF CORRECTION

PATENT NO. : 7,368,593 B1 Page 1 of 1
APPLICATION NO. : 10/920514
DATED : May 6, 2008
INVENTOR(S) : Ramanujam Prasad et al.

It is certified that error appears in the above-identified patent and that said Letters Patent is hereby corrected as shown below:

In the Claims:

At Column 9, line 34, "dialklylarylamines" should be -- dialkylarylamines --.

At Column 9, line 34, "diarylaklylamines" should be -- diarylalkylamines --.

At Column 9, line 39, "dialklylarylamines" should be -- dialkylarylamines --.

At Column 9, line 39, "diarylaklylamines" should be -- diarylalkylamines --.

Signed and Sealed this

Seventeenth Day of February, 2009

JOHN DOLL
*Acting Director of the United States Patent and Trademark Office*